(12) United States Patent
Kamei

(10) Patent No.: US 10,518,100 B2
(45) Date of Patent: Dec. 31, 2019

(54) PHOTIC STIMULATION DEVICE, PHOTIC STIMULATION METHOD, AND PROGRAM

(71) Applicant: NAGASAKI METHOD & CO., LTD., Izumo-shi, Shimane (JP)

(72) Inventor: Tsutomu Kamei, Nagasaki (JP)

(73) Assignee: Nagasaki Method & Co., Ltd., Izumo-shi, Shimane (JP)

( * ) Notice: Subject to any disclaimer, the term of this patent is extended or adjusted under 35 U.S.C. 154(b) by 144 days.

(21) Appl. No.: 15/577,053

(22) PCT Filed: May 28, 2015

(86) PCT No.: PCT/JP2015/065335
§ 371 (c)(1),
(2) Date: Nov. 27, 2017

(87) PCT Pub. No.: WO2016/189719
PCT Pub. Date: Dec. 1, 2016

(65) Prior Publication Data
US 2018/0169430 A1    Jun. 21, 2018

(51) Int. Cl.
*A61N 5/06* (2006.01)
*A61M 21/02* (2006.01)
(Continued)

(52) U.S. Cl.
CPC .............. *A61N 5/06* (2013.01); *A61B 5/048* (2013.01); *A61B 5/04014* (2013.01);
(Continued)

(58) Field of Classification Search
CPC ........ A61N 5/06; A61N 5/0613; A61N 5/062; A61N 5/0622; A61N 5/0624;
(Continued)

(56) References Cited

U.S. PATENT DOCUMENTS 5,191,894 A * 3/1993 Yasushi ................ A61B 5/0484
600/546
5,241,967 A * 9/1993 Yasushi .............. A61B 5/04842
600/27

(Continued)

FOREIGN PATENT DOCUMENTS

EP    0375106 A1   6/1990
JP    H0712378 B2  2/1995
(Continued)

OTHER PUBLICATIONS

Supplementary Partial European Search Report for the Application No. EP15893353, dated Apr. 26, 2018 (10 pages).
(Continued)

*Primary Examiner* — Eugene T Wu
(74) *Attorney, Agent, or Firm* — Lucas & Mercanti, LLP

(57) ABSTRACT

Provided are an photic stimulation device, method, and program, including a waveform generation unit configured to shape a waveform of a frequency band including a part of a band of θ waves and a part of a band of a waves; a pulse modulation unit configured to generate a pulse waveform with duty adjusted on the basis of an amplitude of the waveform generated by the waveform generation unit; and a light exposing unit configured to irradiate a head with a red pulsed beam on the basis of an output of the pulse modulation unit.

14 Claims, 11 Drawing Sheets

(51) Int. Cl.
*A61B 5/0482* (2006.01)
*A61B 5/04* (2006.01)
*A61B 5/048* (2006.01)

(52) U.S. Cl.
CPC ........... *A61B 5/0482* (2013.01); *A61M 21/02* (2013.01); *A61N 5/0622* (2013.01); *A61N 2005/0647* (2013.01); *A61N 2005/0651* (2013.01)

(58) Field of Classification Search
CPC .... A61N 2005/0626; A61N 2005/0645; A61N 2005/0647; A61N 2005/0658; A61N 2005/0662; A61N 2005/0663; A61B 5/04004; A61B 5/04012; A61B 5/04014; A61B 5/04017; A61B 5/0476; A61B 5/048; A61B 5/0482; A61B 5/4064; A61B 5/486; A61B 5/72; A61B 5/7203; A61B 5/7225; A61B 5/7278; A61B 5/6803; A61B 5/6814
See application file for complete search history.

(56) References Cited

U.S. PATENT DOCUMENTS

| | | | |
|---|---|---|---|
| 5,402,797 A * | 4/1995 | Akiyama | A61B 5/0482 600/545 |
| 5,495,853 A | 3/1996 | Yasushi | |
| 5,769,878 A | 6/1998 | Kamei | |
| 5,954,629 A * | 9/1999 | Yanagidaira | A61M 21/00 600/26 |
| 6,129,748 A | 10/2000 | Kamei | |
| 6,537,301 B1 | 3/2003 | Kamei | |
| 2003/0181961 A1 | 9/2003 | Kamei | |

FOREIGN PATENT DOCUMENTS

| | | |
|---|---|---|
| JP | H0984888 A | 3/1997 |
| JP | 2000350784 A | 12/2000 |
| JP | 2001231871 A | 8/2001 |
| JP | 2008178702 A | 8/2008 |

OTHER PUBLICATIONS

Kasper, S., et al. Immunological correlates of seasonal fluctuations in mood and behavior and their relationship to phototherapy, Psychiatry. Res., 36, pp. 253-265 (1991).
International Search Report of Corresponding PCT Application No. PCT/JP2015/065335, dated Aug. 25, 2015. 4 pages.
Terman, M., et al. Light therapy for seasonal affective disorder: a review of efficacy, Neuropsychopharmacology., vol. 2, No. 1, pp. 1-22 (1989).

* cited by examiner

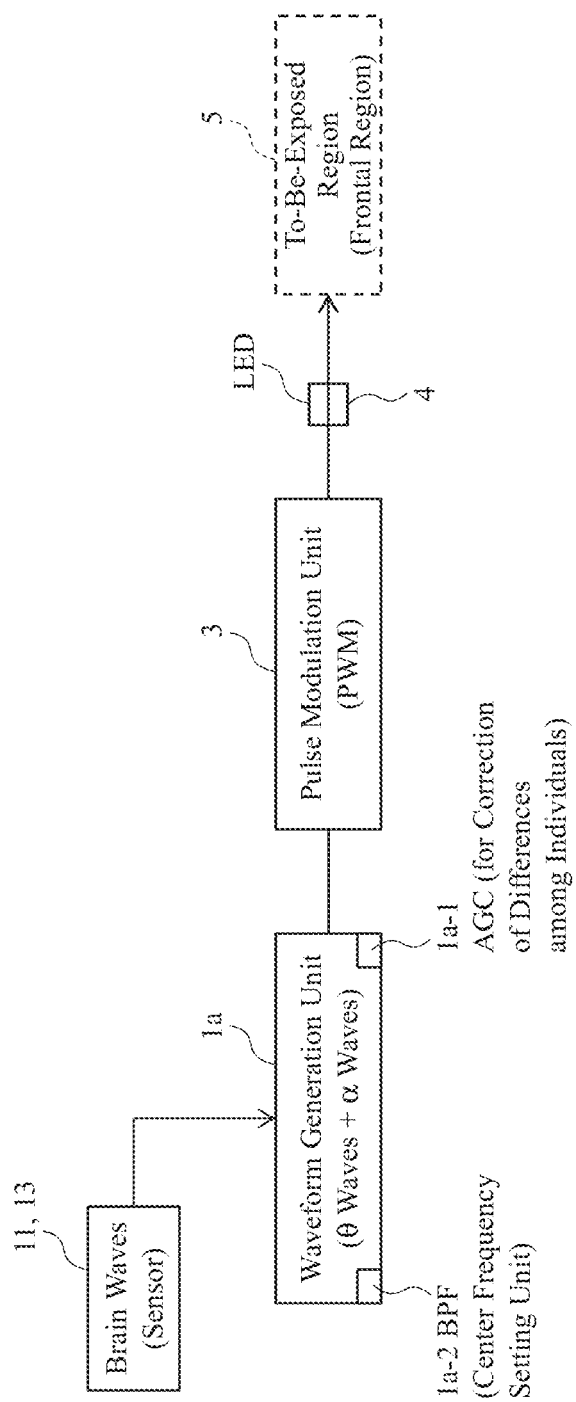

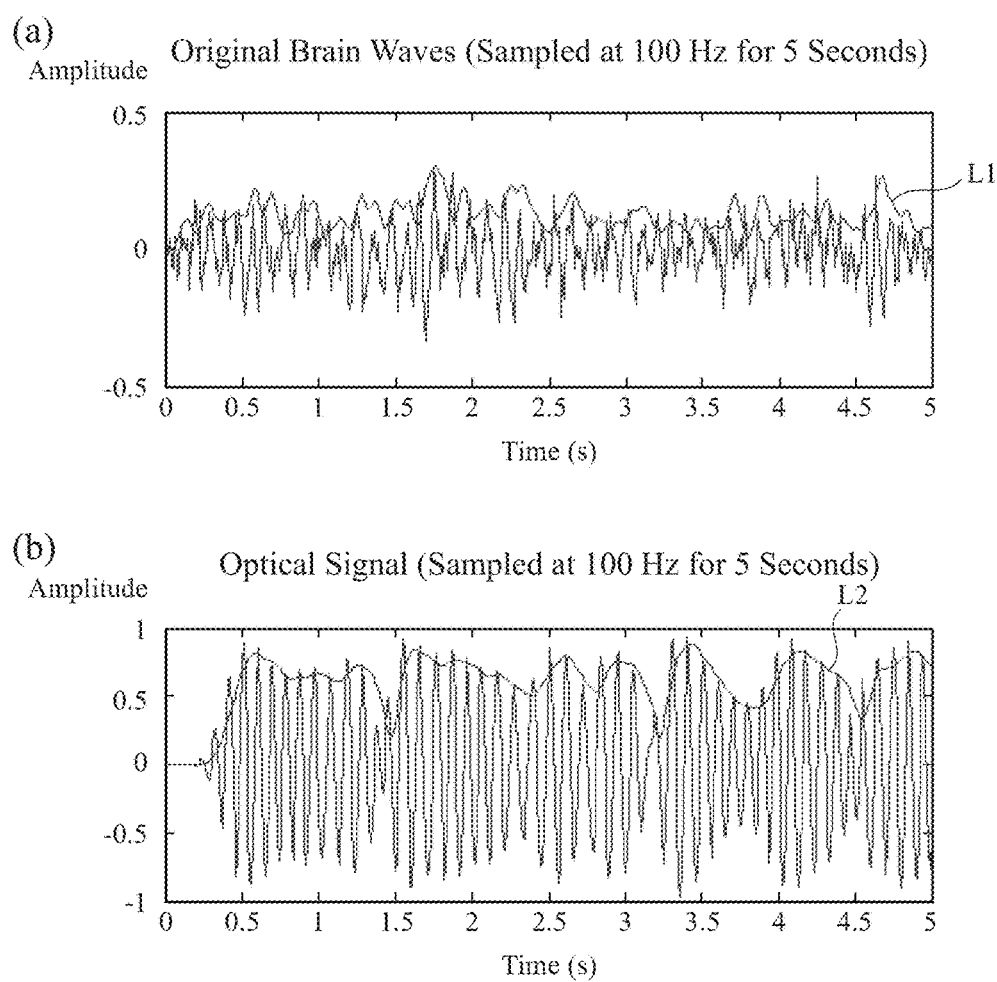

(a)

Output of BPF (Waveform 11))

(b)

Output of Absolute Value (Waveform 12))

(c)

Output of BEF (Waveform 13))

(d)

Output of LPF (Waveform 14))

(a)

(b)

(c)

(a)

(b)

(c)

(d)

PHOTIC STIMULATION DEVICE, PHOTIC STIMULATION METHOD, AND PROGRAM

CROSS-REFERENCE TO RELATED APPLICATIONS

This application is a U.S. national stage of PCT/JP2015/065335 filed on May 28, 2015.

TECHNICAL FIELD

The present invention relates to a photic stimulation technology and, in particular, to a photic stimulation technology for the head.

BACKGROUND ART

As an example of the influence of changes in the light environment in the nature on the immune systems of living organisms, it has been reported that there is recognized a negative correlation between the degree of the unpleasant mood or behavior disorder due to decreased sunshine duration in autumns and winters and the number of natural killer cells (hereinafter referred to as NK cells) in the peripheral blood (see Non Patent Literature 1 below). This report suggests the possibility that continuous light such as sunlight in the daytime may be effectively used for immune regulation. Regarding reactions in the bodies of living organisms to light, it has been said that in birds, reptiles, and fish, for example, light passes through the cranial bones other than the visual pathways and thus directly reacts with the photosensitive cells in the pineal gland. Meanwhile, such reactions have not been known for humans.

When medical effectiveness of light including those other than natural light is considered, medium-wavelength (UVB) or long-wavelength (UVA) ultraviolet rays have been applied to the treatment of skin diseases, such as psoriasis, vitiligo, and atopic dermatitis, while bright light therapy has been applied to the treatment of seasonal affective disorder (SAD), depression, and the like. Meanwhile, near-red light beams have been applied to the treatment of pain, skin ulcer, and the like. Thus, light has been already applied widely, in particular, to clinical medicine. Regarding a medical report of the use of diode light for a light source, basic research that recognized the enhancement of the wound healing effect with the use of light of near-red light-emitting diodes has been conducted so far. Medical usability of light sources with low invasiveness has also been researched.

There have been a number of reports of research on the influence that visible light has on the immune response via the visual pathways, that is, the nervous system. In addition, the inventor has already reported that the activation of $\alpha$ waves in the frontal region that is seen when a healthy subject is optically driven is correlated with the activation of the cell-mediated immunity in the peripheral blood.

However, photic stimulation that is applied via the eyes through optical drive can become a sort of physical stress on the subject. Therefore, it has been considered that such photic stimulation prevents the enhancement of the immune system.

Further, the inventor has proposed technologies for non-invasively enhancing the activity of the brain and immune system by irradiating the head with a light beam from the side of the frontal region while completely shielding the both eyes from the light beam (see Patent Literature 1 and 2).

An irradiation tool described in Patent Literature 1 includes a light source portion adapted to be in contact with the frontal region, and a band portion for mounting (fixing) the light source portion on the head of the user. The inner side of the light source portion (the side of the frontal region of the user) has a number of LEDs arranged therein. A light-shielding portion is provided on the lower edge portion and the side edge portion of the light source portion.

CITATION LIST

Patent Literature

Patent Literature 1: JP 2001-231871 A
Patent Literature 2: JP H09-84888 A

Non Patent Literature

Non Patent Literature 1: S. Kasper, N. E. Rosenthal, S. Barberi, A. Williams, Tamarkin L., S. L. B. Rogers and S. R. Pillemer: *Immunological correlates of seasonal fluctuations in mood and behavior and their relationship to phototherapy*, Psychiatry Res., 36, pp. 253-264 (1991) M. Terman, J. S. Terman, F. M. Quitkin, P. J. McGrath, J. W. Stewart and B. Rafferty: *Light therapy for seasonal affective disorder: a review of efficacy*, Neuropsychopharmacol., 2, pp. 1-22 (1989)

SUMMARY OF INVENTION

Technical Problem

However, the technology described in Patent Literature 1 above has a problem in that since it irradiates the head with a uniform light beam, the resulting effects will greatly vary among individuals.

In view of the foregoing problems, an object of the present invention is to provide a photic stimulation technology that is suited for each individual.

Solution to Problem

According to an aspect of the present invention, there is provided an photic stimulation device, including a waveform generation unit configured to shape a waveform of a frequency band including a part of a band of $\theta$ waves and a part of a band of $\alpha$ waves; a pulse modulation unit configured to generate a pulse waveform with duty adjusted on the basis of an amplitude of the waveform generated by the waveform generation unit; and a light exposing unit configured to irradiate a head with a red pulsed beam on the basis of an output of the pulse modulation unit.

The waveform generation unit is configured to shape the waveform of the frequency band including a part of the band of $\theta$ waves and a part of the band of $\alpha$ waves on the basis of brain waves of an individual.

By irradiating the head, mainly the prefrontal region (frontal association cortex), for example, with a pulsed beam, which has been automatically adjusted on the basis of the frequency and amplitude of the rhythm (fluctuation) of $\alpha$ waves of each individual, it becomes possible to enhance the amplitudes of $\alpha$ waves and $\theta$ waves that are generated spontaneously, thereby non-invasively enhancing nerve impulses in the cerebral cortex and activating the cell-mediated immunity.

Since a red pulsed beam is generated on the basis of a pulsed drive voltage by the pulse modulation unit, it is possible to suppress power consumption and further suppress ripple components in the output voltage and enhance the response performance against load fluctuation. Therefore, damages and the like to the head due to heat can be prevented.

The photic stimulation device further includes a feedback function that reflects a change in the brain waves of the individual occurring upon irradiation of the head with the red pulsed beam by the light exposing unit in a pulsed drive voltage for the light exposing unit. With the feedback function, it is possible to eliminate the need for the frequency sweep process. The feedback function updates data for light irradiation in accordance with a frequency band and an amplitude of the brain waves of the individual.

The frequency band is a continuous frequency band of 7 Hz to 13 Hz.

By irradiating the head, mainly the prefrontal region (frontal association cortex) with a pulsed beam, which has been automatically adjusted on the basis of the rhythm of brain waves of each individual, it becomes possible to enhance the amplitudes of α waves and θ waves that are generated spontaneously, thereby non-invasively enhancing nerve impulses in the cerebral cortex, enhancing the activity of the living organism through changes in the endocrine system, and activating the cell-mediated immunity.

The waveform generation unit has a function of suppressing unevenness in amplitude of brain waves of an individual that have been input.

Accordingly, irradiation with a light beam with an appropriate intensity (duty) is possible.

The photic stimulation device further includes a memory adapted to have stored therein brain waves of an individual or the waveform that has been shaped, and waveform processing is performed on the basis of the waveform read from the memory. Since brain waves need not always be acquired, the process can be simple.

The photic stimulation device further includes a center frequency adjustment unit (BPF unit) configured to adjust the frequency band. By filtering a desired frequency band, more effective results can be obtained.

According to the present invention, there is also provided an photic stimulation device, including a brain-wave amplifier configured to perform A/D conversion on brain waves of an individual acquired with a sensor and amplify the brain waves as appropriate; a control signal generation circuit configured to generate a control signal to control drive of LEDs on the basis of an output signal from the brain-wave amplifier; a pulse width modulation (PWM) unit configured to perform PWM modulation on an output of the control signal generation circuit; and a light exposing unit including the LEDs that are driven on the basis of an output signal from the PWM modulation unit.

The control signal generation circuit includes a first band-pass filter (BPF 1) configured to pass a frequency band including a part of a band of θ waves and a part of a band of α waves, and an automatic gain control (AGC) limiter configured to suppress fluctuation in amplitude of the brain waves that depends on each individual.

The control signal generation circuit further includes a second band-pass filter (BPF 2), and a feedback function of feeding back an output of the second band-pass filter (BPF 2) to the AGC limiter. The photic stimulation device further includes, as circuits that constitute the feedback function: an absolute value circuit configured to output an absolute value of an input; a BEF circuit (Band-Elimination Filter) configured to suppress an amplitude of an input; and an low pass filter (LPF) circuit configured to filter an output of the BEF circuit.

The present invention may also be a tool for an photic stimulation device for irradiating a head of a test subject with the red pulsed beam from one of the aforementioned photic stimulation devices, in which the light exposing unit includes a cap-like member having a number of red LEDs arranged thereon, and an eye protection plate slidably provided on the cap-like member, the eye protection plate is adapted to be, when the head is irradiated with a light beam, slid to a position to cover eyes so as to protect the eyes, and the eye protection plate is adapted to be positioned between the light exposing unit and a to-be-irradiated region when slid back from a direction of the eyes.

The present invention may also be a tool for an photic stimulation device for irradiating a head of a test subject with the red pulsed beam from one of the aforementioned photic stimulation devices, in which the photic stimulation device is provided with a light guide path through which a part of a light beam in a housing of the device is guided to eyes of the test subject as an operation monitoring beam.

The operation monitoring beam can be projected onto the user so that the operation of the light beam that stimulates the brain of the user can be monitored.

The tool further includes an adjustment switch configured to adjust or shield the operation monitoring beam.

In an optical pulse device with an operation check window that is adapted to be mounted on the head and through which light can be adjusted or shielded so as to prevent a too bright light condition or a too dark light condition when the brightness of the external environment has changed outside or inside the room, for example, an operation check display for the device is provided at a visible place, a window through which a part of a photic stimulation signal inside the device can be checked, is provided, an adjustment window for reducing the amount of light is provided on the light guide path, and the operation check window is provided that allows the brightness to be adjusted with the adjustment window operated when the brightness is to be changed.

The adjustment window may be implemented with a pigment with a different transmittance or a shielding object provided on the light guide path. Through the operation check window, the brightness of a check lamp is adjustable, and through a detection window (hole) for detecting the internal optical state, display for checking the brightness and operation is possible.

Start and stop on the system side can also be monitored easily.

According to another aspect of the present invention, there is also provided a photic stimulation method, including a waveform generating step of shaping a waveform of a frequency band including a part of a band of θ waves and a part of a band of α waves; a pulse modulation step of generating a pulse waveform with duty adjusted on the basis of an amplitude of the waveform generated in the waveform generating step; and a light exposing step of irradiating a head with a red pulsed beam on the basis of an output of the pulse modulation step.

The photic stimulation method further includes a feedback process step of reflecting a change in brain waves of an individual occurring upon expose of the head with the red pulsed beam in the light exposing step in a pulsed drive voltage for the light exposing step.

The waveform generating step includes shaping the waveform of the frequency band including a part of the band of θ waves and a part of the band of α waves on the basis of brain waves of an individual. The photic stimulation method further includes a feedback process step of reflecting a change in brain waves of an individual occurring upon exposing of the head with the red pulsed beam in the light exposing step in a pulsed drive voltage for the light exposing step.

The present invention may also be a program for causing a computer to execute the aforementioned photic stimulation method, or a computer-readable recording medium having the program recorded thereon.

Since the head is irradiated with a light beam from LEDs that are driven on the basis of a pulse-modulated drive waveform, it is possible to non-invasively enhance nerve impulses in the cerebral cortex, enhance the activity of the living organism through changes in the endocrine system, and activate the cell-mediated immunity in a state in which the generation of heat is suppressed while taking the individual characteristics into consideration.

Advantageous Effects of Invention

According to the present invention, a photic stimulation technology that is suited for each individual can be provided.

BRIEF DESCRIPTION OF DRAWINGS

FIG. 1A is a functional block diagram showing an exemplary configuration of an photic stimulation device in accordance with the first embodiment of the present invention.

FIG. 3A are diagrams showing examples of the input/output waveforms of a fluctuation waveform generation unit shown in FIG. 1A.

DESCRIPTION OF EMBODIMENTS

Figure 1B:
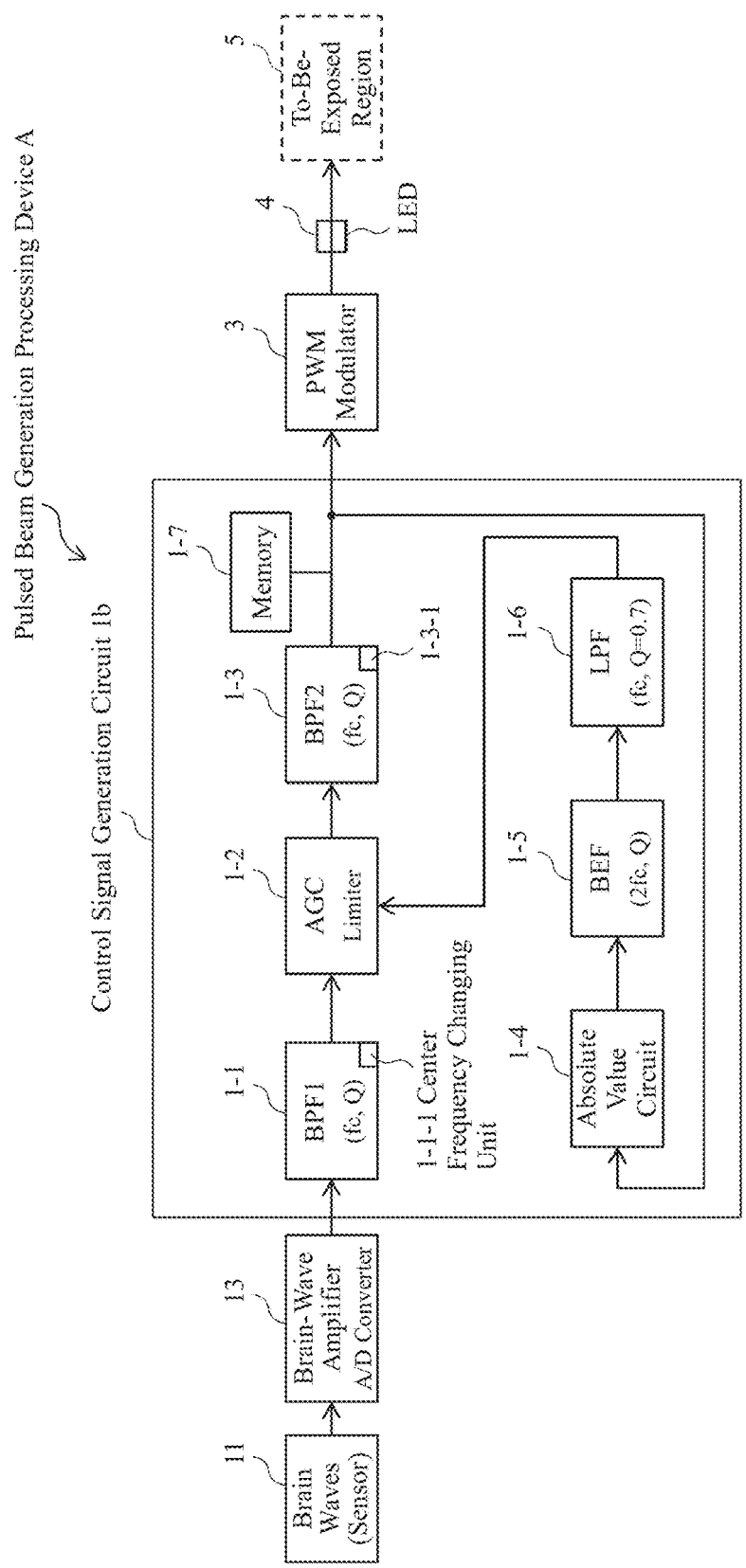
FIG. 1B is a functional block diagram showing an exemplary configuration of an photic stimulation device in accordance with the second embodiment of the present invention.

Hereinafter, embodiments in accordance with the present invention will be described in detail with reference to the drawings. It should be noted that the same reference numerals denote the same members throughout the drawings unless otherwise stated.

Western medicine has no concept of "difference among individuals" or "predisposition." The inventor has been researching a technique for effectively reviving functions that have degraded, taking differences among individuals and predisposition into consideration.

In particular, the inventor conceived of enhancing the amplitudes of α waves and θ waves that are generated spontaneously, by irradiating the head, mainly the prefrontal region (frontal association cortex), for example, with a pulsed beam, which has been automatically adjusted on the basis of the rhythm of brain waves of each individual, thereby non-invasively enhancing nerve impulses in the cerebral cortex, enhancing the activity of the living organism through changes in the endocrine system, and activating the cell-mediated immunity.

Hereinafter, each embodiment of the present invention will be described on the basis of the aforementioned conception.

First Embodiment

First, an photic stimulation device in accordance with the first embodiment of the present invention will be described. It should be noted that in this specification, the head includes the prefrontal region (frontal association cortex) and refers to a region other than the occipital region of the head.

FIG. 1A is functional block diagram showing an exemplary configuration of an photic stimulation device in accordance with the first embodiment of the present invention. The function can be implemented by a hardware configuration, a software configuration, or both. The same holds true hereinafter.

Figure 2:
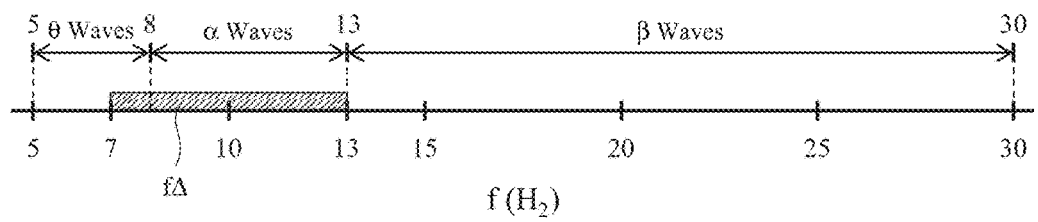
FIG. 2 is a diagram showing an example of the frequency band of brain waves used in this embodiment.

FIG. 2 is a diagram illustrating the frequency band of brain waves used in this embodiment. θ 0 waves have a band of 5 Hz to 8 Hz, α waves have a band of 8 to 13 Hz, and β waves have a band of 13 Hz to 30 Hz.

As shown in FIG. 1A, the photic stimulation device in accordance with this embodiment uses, on the basis of brain waves of a test subject acquired with a sensor 11 (a brain-wave sensor 11 and a brain-wave amplifier 13; hereinafter also referred to as brain waves of an individual), for example, a part of θ waves and a part of α waves of the brain waves, for example, brain waves in a frequency band of 7 Hz to 13 Hz shown in FIG. 2. The photic stimulation device in accordance with this embodiment includes a waveform generation unit 1a that generates an appropriate waveform on the basis of brain waves in the frequency band of an individual, a pulse modulation unit 3 that performs pulse modulation (PWM modulation) on the output of the waveform generation unit 1a, and a light exposing unit 4, such as red light-emitting diodes driven on the basis of the pulse-modulated drive waveform (for example, LEDs with a light emission wavelength of 660 nm). The wavelength of the red light source for the light exposing unit 4 is preferably in the range of 610 nm to 750 nm. A red pulsed beam emitted from the light exposing unit 4 irradiates a to-be-irradiated region 5 of the test subject, such as the head. Although the waveform generation unit 1a has been described as generating an appropriate waveform on the basis of brain waves of an individual, the target for which a waveform is generated is not limited to brain waves of an individual. For example, brain waves of close relatives or patients with a similar disease can also be used.

It should be noted that the waveform generation unit 1a may also include, for example, an AGC unit 1a-1 that suppresses differences in amplitude among individuals, and a BPF unit 1a-2 that extracts only the waveforms of predetermined frequency bands of α waves and θ waves. The detailed configurations of such units will be described in detail in the second embodiment.

FIG. 3A are diagrams showing examples of an input signal of brain waves (original brain waves (a)) input to the waveform generation unit 1a and an output signal (b) from the waveform generation unit 1a, where the ordinate axis indicates the amplitude, and the abscissa axis indicates time (s). Both the signals are sampled at 100 Hz. Symbols L1 and L2 indicate the envelopes of the respective waveforms.

Figure 3B:
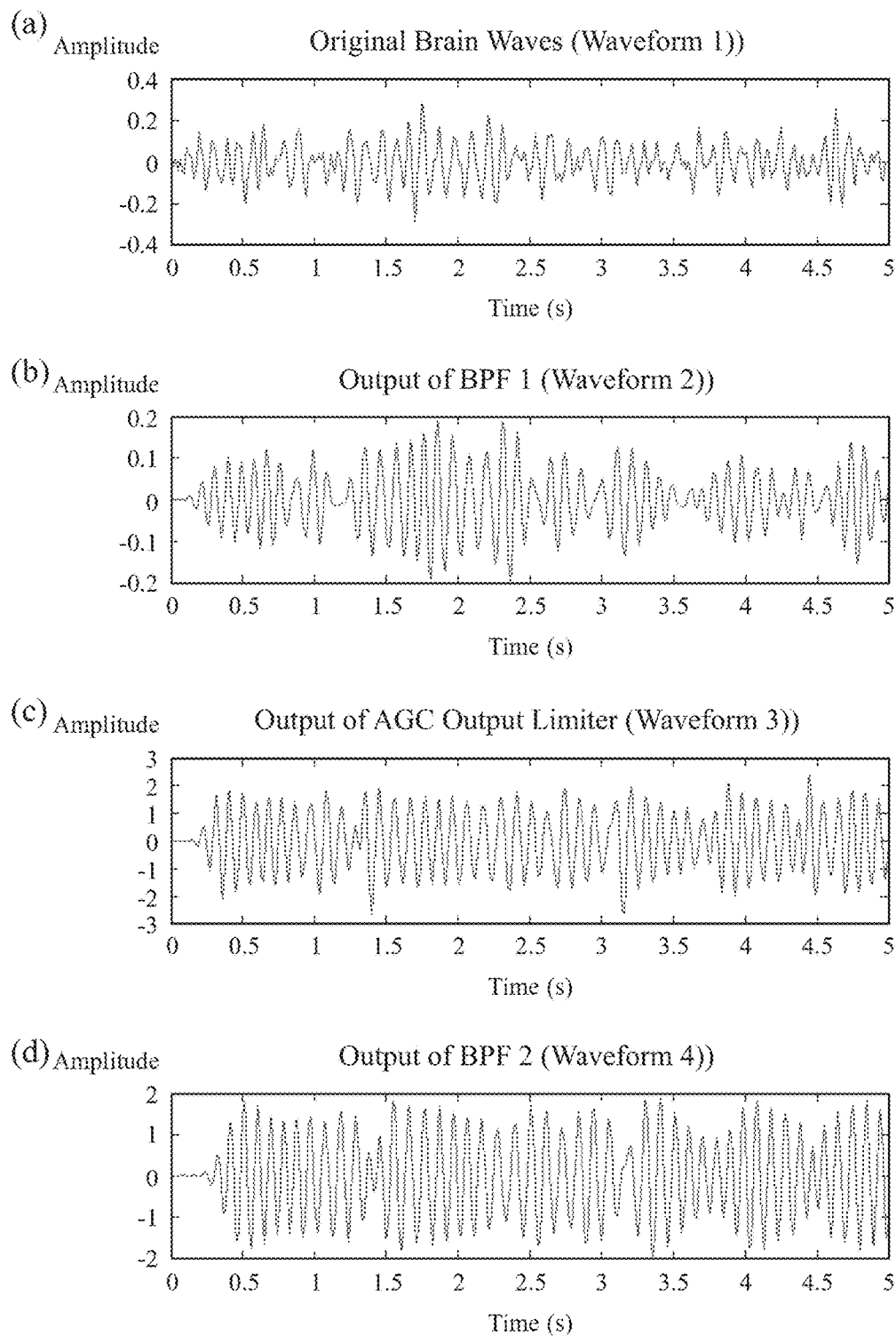
FIG. 3B are diagrams showing exemplary transitions of the waveforms of the circuits shown in FIG. 1B.

As shown in FIGS. 3A and 3B, a process of deforming a waveform so as to absorb (eliminate) individual singularity while retaining individual fluctuation is performed as can be seen from the comparison between the envelopes L1 and L2.

As described above, with the photic stimulation device in accordance with this embodiment, a waveform with frequency fluctuation that is based on brain waves of an individual is created, and the head of the individual is irradiated with a light beam from red LEDs that are driven on the basis of a drive waveform generated through pulse modulation of the created waveform. Therefore, it is possible to remove individual singularity while taking the individual characteristics into consideration and further noninvasively enhance nerve impulses in the cerebral cortex, enhance the activity of the living organism through changes in the endocrine system, and activate the cell-mediated immunity while suppressing the generation of heat through the pulse modulation.

It should be noted that the LEDs are not limited to red LEDs, and the frequency band is not limited to 7 Hz to 13 Hz. Further, the light source is not limited to the one using LEDs.

Second Embodiment

Next, the second embodiment of the present invention will be described in detail. FIG. 1B is a functional block diagram showing an exemplary configuration of aphotic stimulation device in accordance with this embodiment, and corresponding to FIG. 1A.

When a drive voltage for a pulsed beam is generated on the basis of brain waves of an individual, if photic stimulation applied is too strong, a stimulus applied to the body becomes too strong, while if photic stimulation applied is too weak, the resulting effect becomes too small.

As shown in FIG. 1B, the photic stimulation device in accordance with this embodiment includes the brain-wave amplifier 13 that performs A/D conversion on brain waves of a test subject acquired with the sensor 11 and amplifies the brain waves as needed; a control signal generation circuit 1b that generates a control signal for controlling the drive of the LEDs on the basis of an output signal from the brain-wave amplifier 13; the PWM modulation unit 3 that performs PWM modulation on the output of the control signal generation circuit 1b; and the light exposing unit 4 with red LEDs that are driven on the basis of an output signal from the PWM modulation unit 3. A light beam from the light exposing unit 4 irradiates the to-be-irradiated region 5 of the test subject, for example, the head, as a pulsed beam. The PWM modulation unit 3 does not change the frequency but represents the waveform on the basis of the width and sign (positive or negative) of a variable pulse. Accordingly, ripple components of the output voltage can be suppressed and response performance against load fluctuation can be increased. It is also possible to use PFM modulation instead of PWM modulation.

The control signal generation circuit 1b includes, for example, a first band-pass filter (BPF 1) 1-1, an AGC limiter 1-2, and a second band-pass filter (BPF 2) 1-3.

Further, the control signal generation circuit 1b includes, as a feedback function for feeding back the output of the second band-pass filter (BPF 2) 1-3 to the AGC limiter 1-2, an absolute value circuit 1-4, a BEF circuit 1-5 that outputs a frequency double the frequency of its input, and an LPF circuit (fc, quality factor Q=0.7) 1-6 that filters the output of the BEF circuit 1-5. The first band-pass filter (BPF 1) 1-1 can also be allowed to function as a center frequency changing unit 1-1-1 that changes the center frequency in the range of 5 Hz to 15 Hz as appropriate. The BEF circuit 1-5 is a band-elimination filter that eliminates only given frequencies and passes other frequencies.

Further, a memory 1-7 that stores the output of the second band-pass filter (BPF 2) 1-3 may also be provided.

Figure 1C:
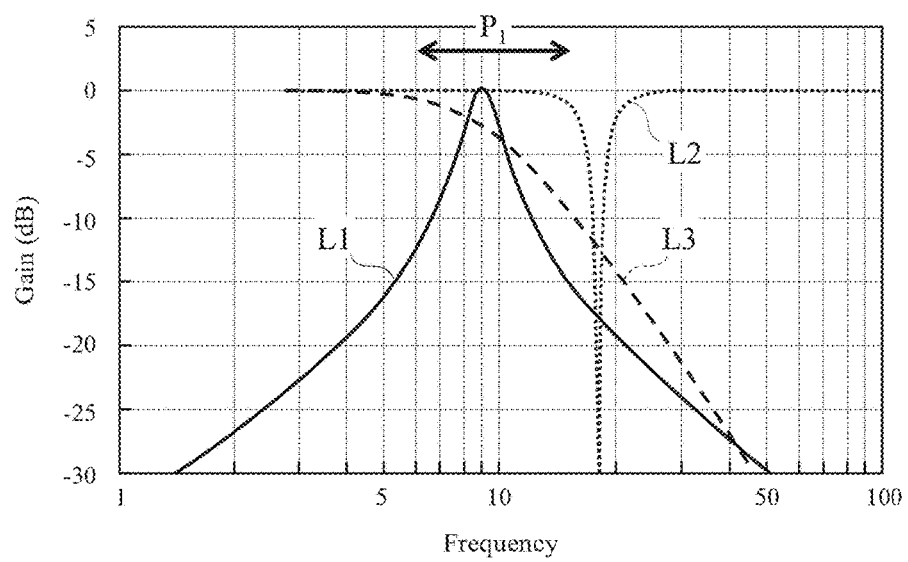
FIG. 1C is a diagram showing exemplary characteristics of BPF, AGC control notch, and LPF.

FIG. 1C is a diagram exemplary showing the frequency characteristics L1 of the BPF, the AGC control notch L2 of the AGC limiter 1-2, and the frequency characteristics L3 of the LPF 1-6. The characteristics in this example correspond to those when the center frequency fc=9.0 Hz and Q=5.

With such characteristics, the control signal generation circuit 1b can output a processed signal, which is based on brain waves in the frequency range indicated by reference numeral P1, to the PWM modulation unit 3.

FIG. 3B are exemplary diagrams in which waveforms processed with the circuits shown in FIG. 1B are shown based on the relationship between the frequency and amplitude.

A waveform 1) shown in FIG. 3B(a) is an example of a waveform input to the first band-pass filter (BPF 1) 1-1, where the ordinate axis indicates the amplitude and the abscissa axis indicates the sampling time. For example, the waveform 1) is a first waveform obtained by amplifying brain waves of an individual.

A waveform 2) shown in FIG. 3B(b) is an exemplary output waveform of the first band-pass filter (BPF 1) 1-1. For example, only a wavelength of 7 Hz to 13 Hz such as the one shown in FIG. 2 is extracted from the first waveform 1).

A waveform 3) shown in FIG. 3B(c) is the output waveform of the AGC limiter 1-2 that receives the waveform 2) as an input. In the output waveform, fluctuation in amplitude dependent on the individual is suppressed.

A waveform 4) shown in FIG. 3B(d) is an exemplary output waveform of the second band-pass filter (BPF 2) 1-3 that receives the waveform 3) as an input. The BPF 2 (1-3) is provided as appropriate to perform a waveform shaping process.

Accordingly, it is possible to suppress differences among individuals while retaining differences in the waveform among individuals and obtain a waveform that can be easily shaped into a pulsed signal.

It should be noted that the waveforms 3) and 4) are exemplary waveforms that are obtained when the feedback function described below is made active.

Figure 3C:
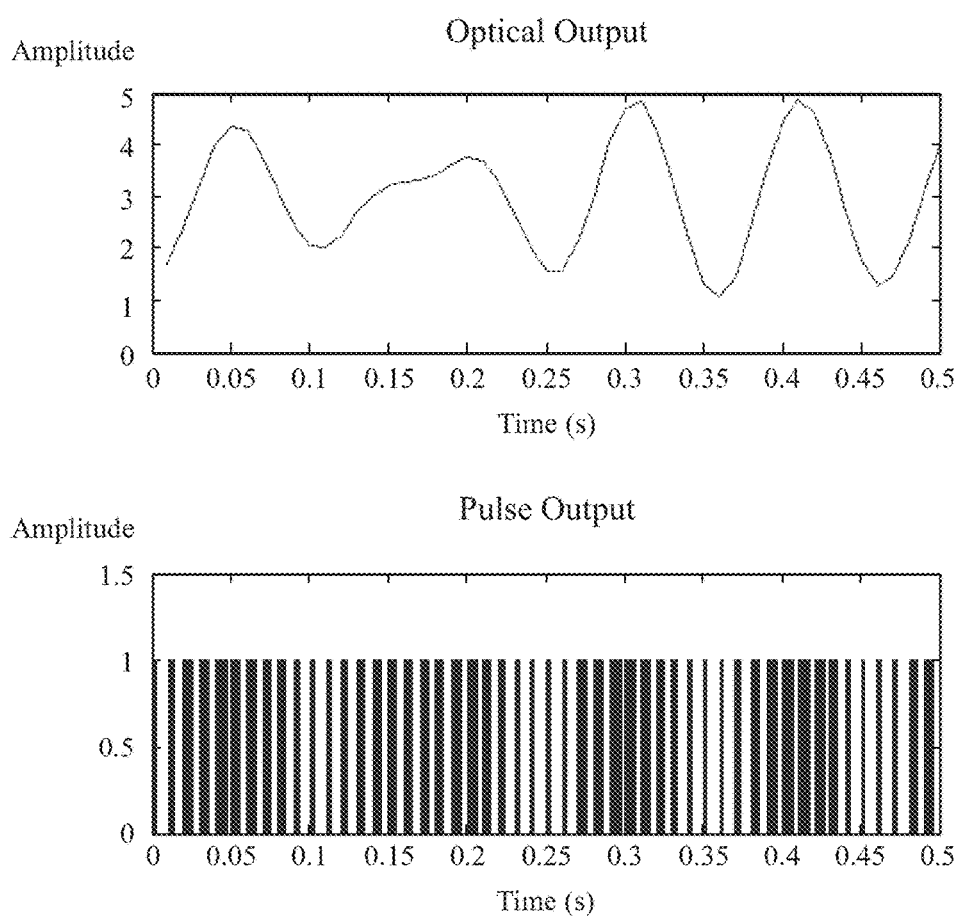
FIG. 3C are diagrams showing the input waveform (a) and the output waveform (b) of a pulse modulation unit.

FIG. 3C indicate the input/output waveforms of the PWM circuit 3 that receives the waveform 4) as an input, where the scale of the abscissa axis is changed. In accordance with the period (frequency) and amplitude of the waveform 4) in FIG. 3B(d) shown in FIG. 3C(a), the duty of a pulsed waveform is adjusted as shown in FIG. 3C. Accordingly, a pulsed waveform can be obtained in accordance with the waveform 4) with the PWM circuit 3. When such a pulsed waveform is used as the drive voltage for the LEDs 4, the generation of heat can be suppressed.

Figure 3D:
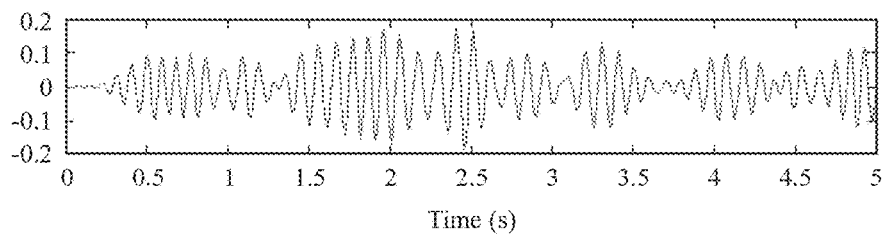
FIG. 3D are diagrams showing exemplary transitions of waveforms in a feedback circuit shown in FIG. 1B.
Figure 3D:
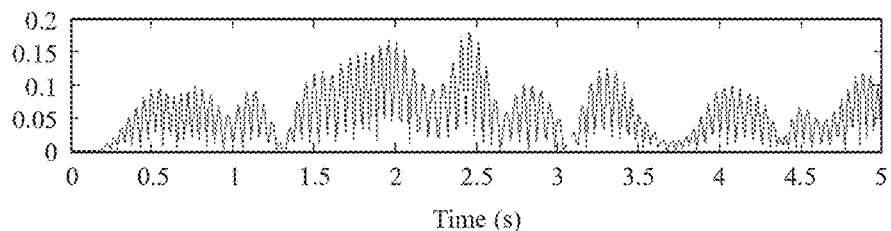
Figure 3D:
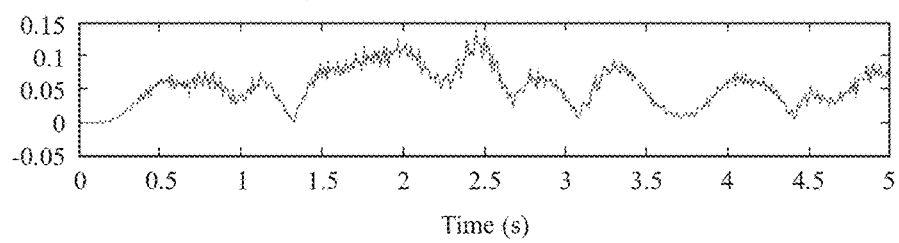
Figure 3D:
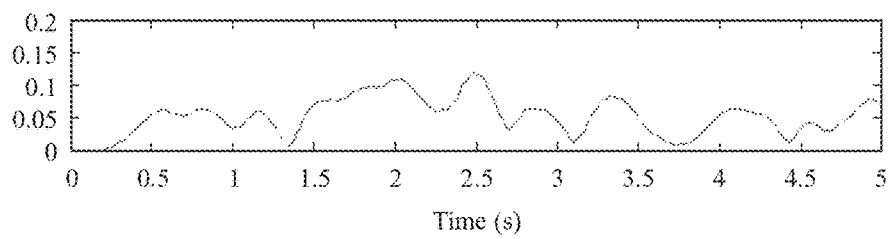

FIG. 3D show exemplary waveforms processed with the feedback circuit in FIG. 1B.

A waveform 11 is an output waveform of the second band-pass filter (BPF 2) 1-3.

A waveform 12) shows an example in which the absolute value of the waveform 11) is determined by the absolute value circuit 1-4. Accordingly, the amplitude of the waveform can be easily calculated.

A waveform 13) shows an example in which the amplitude of the waveform 12) is suppressed by the BEF circuit 1-5 based on the characteristics of the control notch shown in FIG. 1C.

A waveform 14) is an example in which the amplitude of the waveform 13) is multiplied by 0.7, for example, by the LPF 1-6 with the baseline of the amplitude set to zero.

When the waveform 14) is input to a control terminal of the AGC limiter 2, the amplitude dependent on differences among individuals is fed back to the AGC limiter circuit 1-2. Therefore, it is possible to suppress fluctuation while retaining the characteristics of the individuals.

Modified Example

For example, a waveform that has some effects on an individual may be stored in the memory 1-7 that stores the output of the second band-pass filter (BPF 2) 1-3 so that a pulsed signal may be generated using the waveform from the memory thereafter. Alternatively, brain waves may be stored in the memory. Besides, an output of one or more of the circuits shown in FIG. 1B may be stored in the memory so that the process can be simplified.

Third Embodiment

Figure 4:
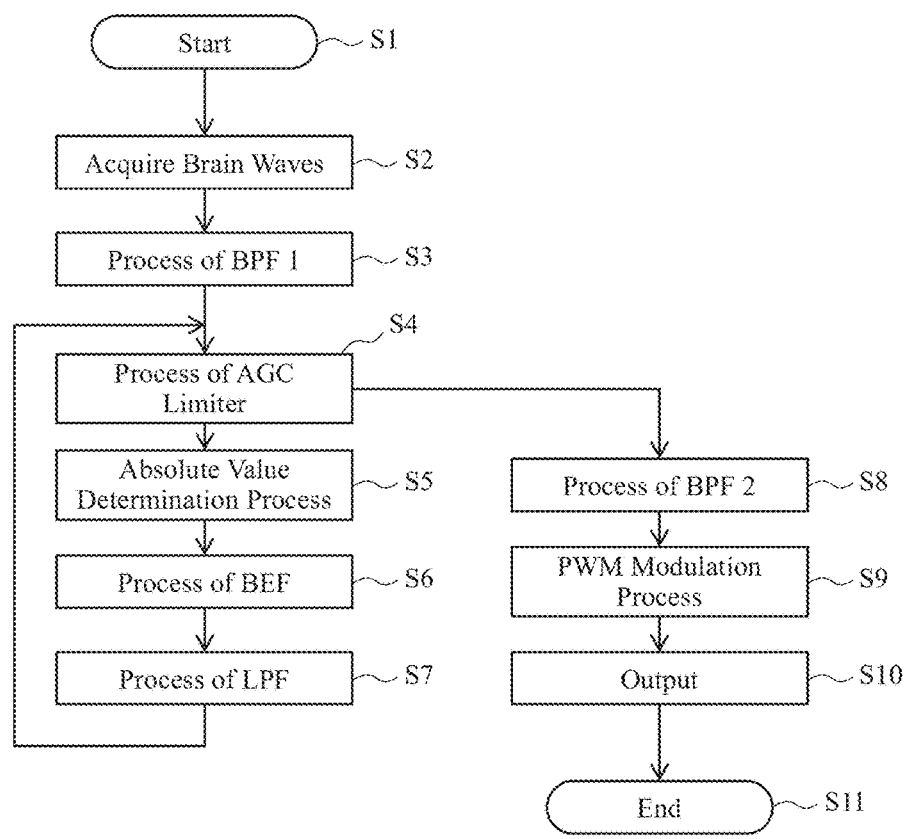
FIG. 4 is a flowchart showing an exemplary flow of waveform processing.

FIG. 4 is a flowchart showing a flow of the aforementioned process in accordance with the first and second embodiments when the process is performed using software as the third embodiment of the present invention. As shown in FIG. 4, first, when a process is started (Start), brain waves are acquired in step S2. Next, the process of the BPF 1 is performed in step S3, and the process of the AGC limiter is performed in step S4. Next, the absolute value determination process is performed in step S5, the process of the BEF is performed in step S6, the process of the LPF is performed in step S7, and the processing results are returned to step S4. Next, the process of the BPF 2 is performed in step S8, and the PWM modulation process is performed in step S9, Then, a pulsed drive voltage is applied to the LEDs in step S10, and the process is terminated (step S11).

Fourth Embodiment

Figure 5:
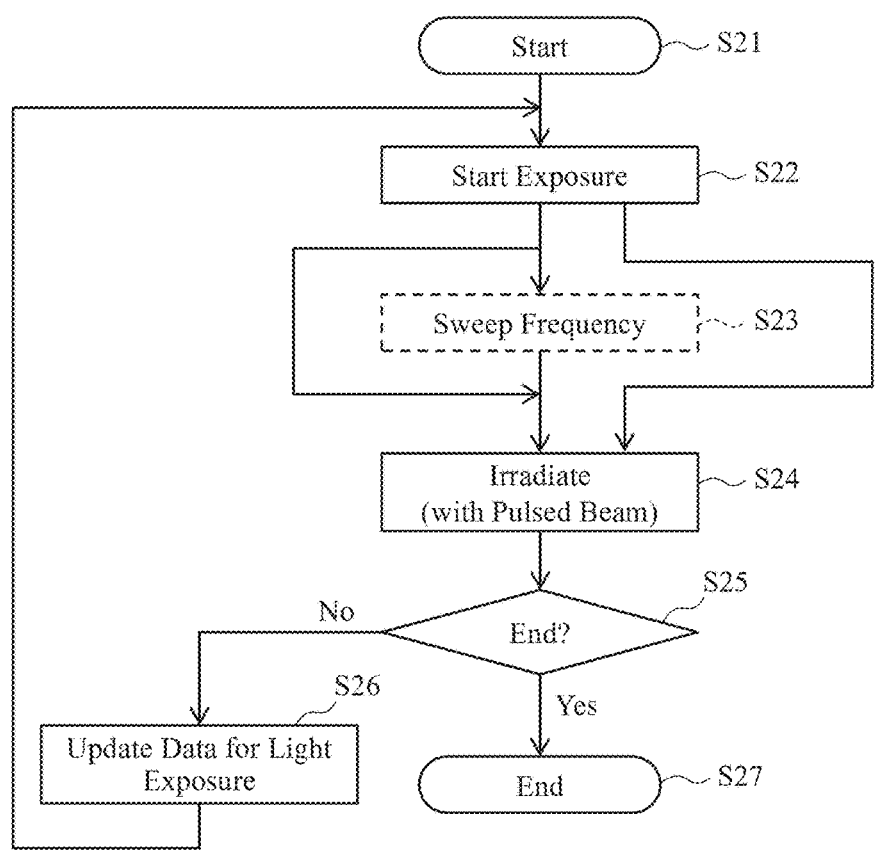
FIG. 5 is a flowchart showing a flow of a process of irradiating the head with a light beam.

FIG. 5 is a flowchart showing, as the fourth embodiment of the present invention, a flow of a process of irradiating the head of a test subject with a light beam from LEDs that are driven on the basis of a LED-driving pulsed signal in each of the first to third embodiments.

In step S21, a photic pulse exposing process is started (Start), and in step S22, the actual light exposing is started. Herein, a frequency sweep process of about 3 minutes may be performed as in step S23. As the frequency sweep process, exposing is performed at regular intervals (at intervals of about 3.5 seconds) in decrements of 0.1 Hz in the range of 13 Hz to 7 Hz, for example.

Next, in step S24, the head is irradiated with a pulsed beam. The exposing time is about 12 minutes, for example. Until it is determined that 12 minutes have elapsed with a time counter in step S25, data for light exposing is updated in step S26 so that the flow returns to step S22. The process of updating data for light exposing is, like the process shown in FIG. 4, a feedback process of reflecting the processing results of FIG. 4, which are based on brain waves that have changed upon optical pulse exposing, in the pulsed drive voltage for the LEDs. The exposing time is preferably 12 minutes (with sweep) to 15 minutes (without sweep), for example.

For example, based on the frequency region of brain waves of an individual, the data updated next is configured to irradiate the head with an optical pulse only for the frequency region detected as the brain waves of the individual. In addition, the amplitude is also updated in accordance with the amplitude detected as the brain waves of the individual. For example, the amplitude is increased if the detected amplitude is large, and is reduced if the detected amplitude is small. Such a feedback process can eliminate the need fir the frequency sweep process.

Fifth Embodiment

Figure 6:
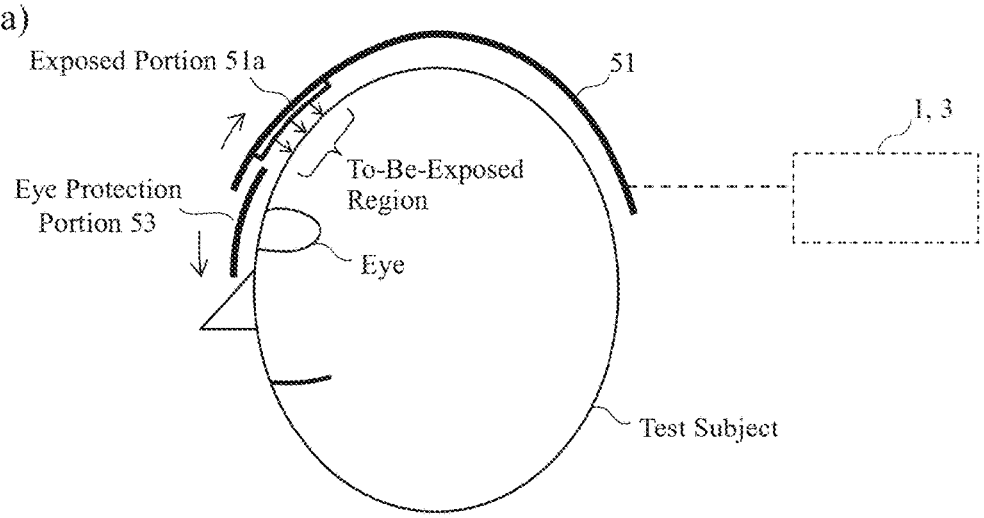
FIG. 6 are diagrams showing an exemplary configuration of a light exposing device in accordance with an embodiment of the present invention.
Figure 6:
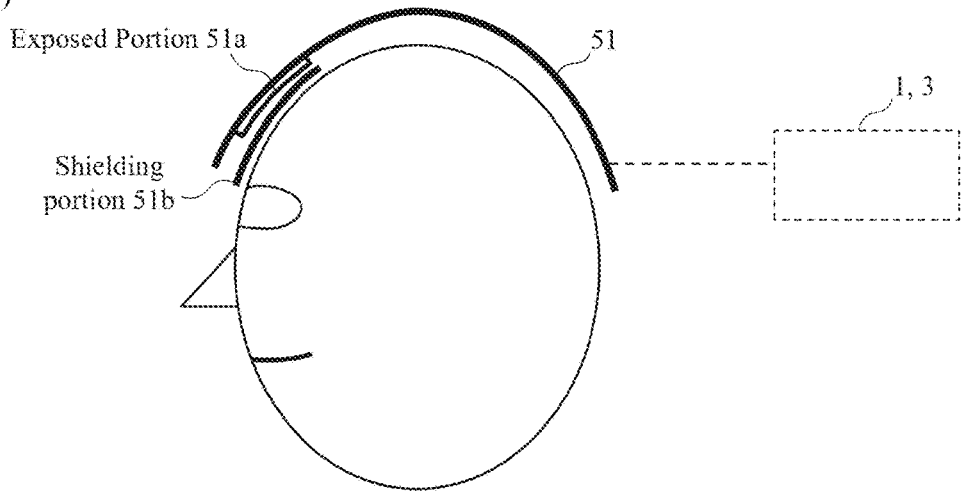
Figure 6:
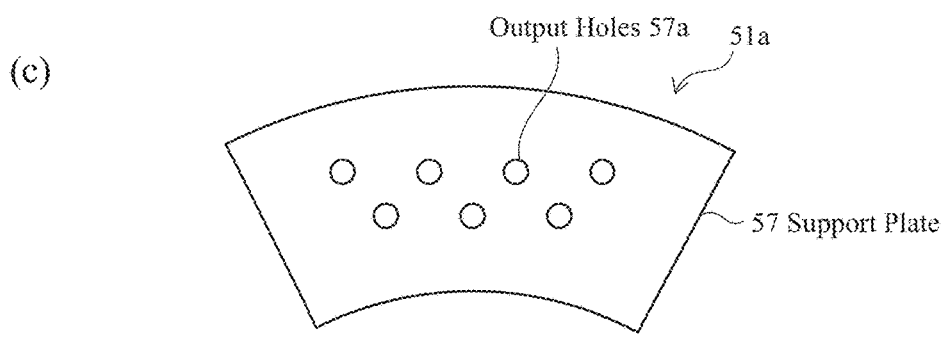

FIG. 6 are diagrams showing an exemplary configuration of an photic stimulation device in accordance with the fifth embodiment of the present invention, and showing an exemplary tool for irradiating the head of a test subject with a red pulsed beam obtained through the process in accordance with each of the first to fifth embodiments. As shown in FIG. 6(c), the head is covered with a cap-like member 51 with a support plate 57, which has a number of LEDs 4 (not shown) at the positions of output holes 57a, provided on its rear surface (a to-be-irradiated region on the side of the head).

The head is irradiated with a red light beam on the basis of a pulsed drive voltage generated by the waveform generation unit 1a, the pulse modulation unit 3 (FIG. 1A), and the like. Herein, an exposing portion 51a of the cap-like member 51 is positioned such that it coincides with the to-be-irradiated region. Then, when the head is actually irradiated with a light beam, an eye protection portion 53 slidably provided on the cap-like member 51 is slid down to the positions of the eyes so as to protect the eyes (FIG. 6(a)).

As shown in FIG. 6(b), the eye protection portion 53 is configured to be, when slid back from the positions of the eyes, positioned between the exposing portion 51a and the to-be-irradiated region, and can protect the eyes by shielding light from the exposing portion 51a.

Accordingly, in this embodiment, the light irradiation and the protection of the eyes can be performed effectively.

Sixth Embodiment

Figure 7:
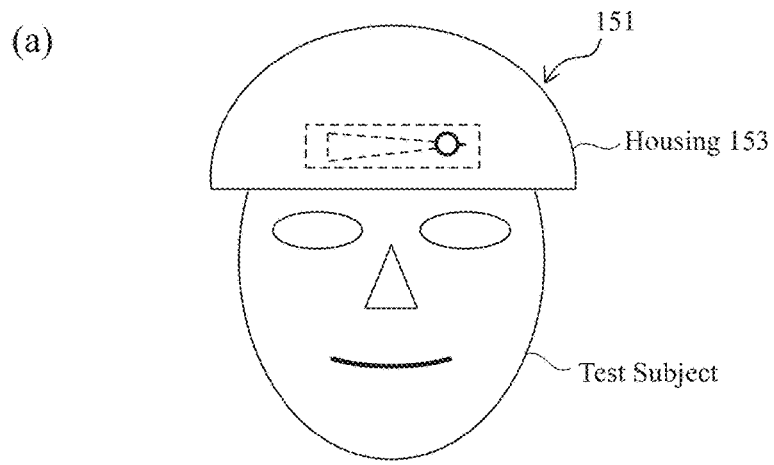
FIG. 7 are diagrams showing an exemplary configuration of an photic stimulation device in accordance with the sixth embodiment of the present invention, and showing another example of a tool for irradiating the head of a test subject with a red pulsed beam that has been obtained through a process in accordance with each of the first to fifth embodiments.
Figure 7:
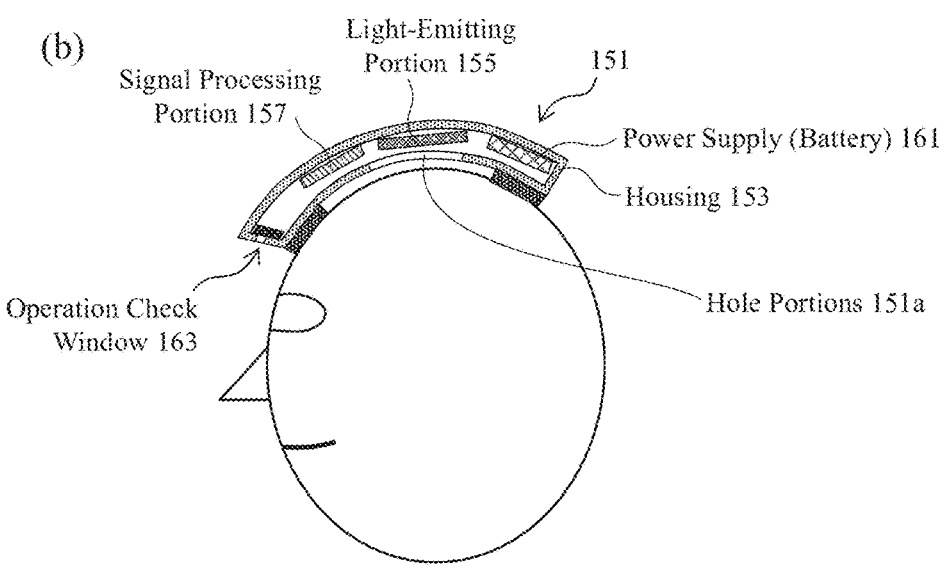
Figure 7:
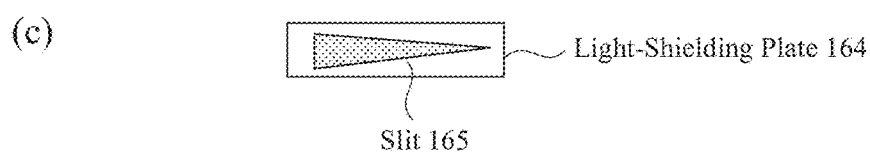
Figure 7:
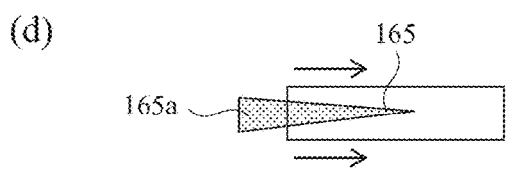

FIG. 7 are diagrams showing an exemplary configuration of an photic stimulation device in accordance with the sixth embodiment of the present invention, and showing another exemplary tool for irradiating the head of a test subject with a red pulsed beam obtained through the process in accordance with each of the first to fifth embodiments.

In an optical pulse device 151 adapted to be mounted on the head shown in FIGS. 7(a) and (b), a signal processing portion 157 and a power supply (battery and the like) 161, for example, are arranged in the housing 153 of the device in addition to a light-emitting portion 155. The signal processing portion 157 and the power supply (battery and the like) 161 may also be arranged outside the housing 153.

In the aforementioned configuration, in order to easily monitor the operation (start or stop) of a light beam to stimulate the brain, there is provided a function of projecting an operation monitoring beam onto the user by guiding a part of a light beam in the housing 153 to a place where the light beam reaches the eyes of the user.

As described above, in the optical pulse device 151 adapted to be mounted on the head, a window 163, through which a part of a photic stimulation signal in the device can be checked, for checking the operation of the device, is provided at a visible place. In addition, an adjustment window for reducing the amount of light is provided on the light guide path leading to the eyes so that when the user wants to change the brightness, he/she can adjust the brightness by operating the adjustment window.

The adjustment of light with the adjustment window 163 may be implemented by using a pigment with a different transmittance or a shielding object provided on the light guide path, and may be implemented with any device that adjusts the brightness of a check lamp through the operation check window.

For example, as shown in FIGS. 7(c) and 7(d), such a function includes the operation check window 163, and an adjustment switch function is also provided so that an operation monitoring beam can be adjusted or shielded.

The adjustment switch function includes a slit 165 provided at a position facing the operation check window 163, and a light-shielding plate 164 disposed so as to be able to adjust the aperture range of the slit 165 as shown in FIGS. 7(c) and 7(d), for example. By sliding the light-shielding plate 164 to adjust the aperture range of the slit 165, it is possible to adjust or shield light so as to prevent a too bright condition or a too dark condition when the brightness of the external environment has changed outside or inside the room, fir example.

As described above, according to the present embodiment, a detection window (hole) for detecting the optical state inside the device is provided to implement brightness check display and operation check display, and thus, monitoring that facilitates the start and stop on the system side is made possible.

The processes and control can be implemented through software processing by means of a CPU (Central Processing Unit) or a GPU (Graphics Processing Unit) or through hardware processing by means of an ASIC (Application Specific Integrated Circuit) or an FPGA (Field Programmable Gate Array).

With the device of the present invention, functions of a human brain that have degraded can be revived. Specifically, according to the present invention, the amplitudes of α waves and θ waves that are generated spontaneously are enhanced through exposing of the head, mainly the prefrontal region (frontal association cortex), with a pulsed beam, which has been automatically adjusted on the basis of the rhythm of brain waves of each individual, whereby it becomes possible to non-invasively enhance nerve impulses in the cerebral cortex, achieve relaxation through changes in the endocrine system, and activate the cell-mediated immunity.

In the evolution process of humans, changes (evolution) in organs (including skeletons) occur to protect very important parts (in particular, to protect against physical factors related with ones' livings; it is considered that species or subspecies that have evolved in accordance with the environment in such a way have been naturally selected and existed so far.) In return (for the evolution), functions related with inherent physiological activation or adjustment may gradually degrade in some cases. The present invention is said to be a typical example of a technology for reviving such physiological and immunological functions that could not help degrading.

The device of the present invention further allows for, by stimulating the head of a human, mainly the prefrontal region (frontal association cortex), in particular, with a red pulsed beam in a particular wavelength range, enhancement and further, prevention of fluctuation in frequency and amplitude of α waves, which would otherwise result from distortion in the living organism that exceeds the range of the rhythm (fluctuation) of a physiological phenomenon, by tuning and amplifying the frequency and amplitude to those in the range of a part of the band of θ waves to a part of the band of α waves of each individual. Such photic stimulation of the head causes revival of the photosensitive function of the brain surface (mainly, the cerebral cortex) that has degraded and promotes excitation of the neurons in the cerebral cortex, thereby enhancing nerve impulses (alleviating mental stress through changes in the endocrine system) and activating the innate immune system (cell-mediated immunity). This enhances the immunological surveillance capability and is estimated to attack and defend against virus-infected cells or cancer cells (even a healthy subject is said to have 3,000 to 5,000 cancer cells generated therein each day).

The immune system is classified into the acquired immune system and the innate immune system (cell-mediated immunity). With the acquired immune system, upon intrusion of foreign matter such as bacteria or viruses into the human body, antigen-presenting cells, such as dendritic cells, present antigens to helper T cells to transmit information on the foreign matter thereto, so that the helper T cells instruct B cells to form antibodies for the antigens and the antibodies, in turn, attack and destroy the foreign matter. Meanwhile, the innate immune system (cell-mediated immunity) is the immune system for, immediately before the acquired immune system acts, initially defending against the foreign matter by means of NK cells, macrophages, and granulocytes (neutrophils) that are patrolling so as to be able to instantly attack the foreign matter. Photic stimulation of the head with the device of the present invention is characterized by activating NK cells. It should be noted that an increase in the number of NK cells can be confirmed by measuring, for CD 57 and CD 16 that are cell surface antigens of NK cells in the peripheral blood (herein, CD is the abbreviation of "Cluster of Differentiation"), the number of $CD57^-CD16^+$ cells and $CD57^+CD16^+$ cells using flow cytometry or the like.

It has been known that immunity can be boosted by controlling α waves of human brains. In particular, the activation of NK cells or relaxation effect by means of photic stimulation with a pulsed beam with a frequency of 0.5 Hz to 13 Hz, in particular, is also described in JP H09-84888 A, JP 2001-231871 A, and the like by the inventor. However, as described above, such techniques are adapted to irradiate the head with a uniform light beam and do not take differences among individuals or predisposition into consideration, and thus there has been a problem in that the resulting effects have a big difference among individuals. In human brain waves, α waves (with a frequency of 13 Hz to 8 Hz) appear when he/she is at rest and closing his/her eyes and θ waves (with a frequency of 7 Hz to 4 Hz) appear when he/she is in a light sleep. When he/she is in the waking state, β waves (with a frequency of 30 Hz to 14 Hz) become dominant, and thus he/she is influenced by tension and stress. The device of the present invention allows for enhancement of the amplitudes of brain waves in parts of the bands of θ waves and α waves (typically, 7 Hz to 13 Hz, preferably, 7 Hz to 12 Hz, or more preferably, 7 Hz to 10 Hz) that are generated spontaneously, by irradiating the head, mainly the prefrontal region (frontal association cortex) with a red pulsed beam (any wavelength in the range of 610 nm to 750 nm is used) whose frequency and amplitude have been automatically adjusted to those of the rhythm of a waves of each individual obtained through measurement of his/her brain waves. Actually, through exposing of each of healthy subjects, cancer patients, the elderly, and the like with a red pulsed beam in accordance with the present invention, for example, 1 to 6 times a day (in case of 4 to 6 times a day, exposing is conducted at a break time (interval) of 15 minutes or longer between the first and second exposing in the morning, and such set of exposing is also conducted once or twice in the afternoon) such that each exposing is conducted for 15 minutes and continued for a period of about 2 to 3 weeks or longer, it has been confirmed that nerve impulses in the cerebral cortex are enhanced (the cerebral cortical function is activated), the activity of the living organism is enhanced through changes in the endocrine system (for example, irritation or mental stress is eased with a reduction in the level of norepinephrine (noradrenaline) in the blood, and the innate immune system (cell-mediated immunity) is activated (for example, the activity of NK cells is enhanced).

By reviving photosensitivity that has been inherently present on the brain surface (a portion that is embryologically called "telencephalon") using the technology of the present invention, it is possible to revive a part of the physiological functions that are degrading in brains of modern humans (for example, enhance nerve impulses in the cerebral cortex, enhance the activity of the living organism through changes in the endocrine system, and activate the cell-mediated immunity). Through a series of researches conducted by the inventor based on mutual cooperation of medical and engineering sciences, it has become possible to revive the photosensitivity of the cerebral cortex and thus revive the natural healing ability.

In the aforementioned embodiments, configurations and the like that are shown in the attached drawings are not limited thereto, and can be changed as appropriate within the range that the advantageous effects of the present invention can be exerted. Further, the configurations and the like can be changed as appropriate without departing from the scope of the object of the present invention.

Further, the configurations of the present invention can be freely selected, and an invention that includes the selected configurations is also included in the present invention.

INDUSTRIAL APPLICABILITY

The present invention is applicable to optical pulse exposing devices for the head.

REFERENCE SIGNS LIST

1a Waveform generation unit
3 (PWM) pulse modulation unit
4 Light exposing unit (LED)
11 Brain-wave sensor
13 Brain-wave amplifier
51 Cap-like member
51a Exposing portion
51b Shielding portion
53 Eye protection portion
57 Support plate
57a Output hole All publications, patents, and patent applications cited in this specification are all incorporated by reference into this specification.

The invention claimed is:
1. A photic stimulation device for a head comprising:
a brain wave amplifier configured to perform A/D conversion on brain waves of an individual acquired with a sensor and amplify the brain waves;
a control signal generation circuit configured to generate a control signal to control drive of LEDs on the basis of an output signal from the brain wave amplifier; and
a light exposing unit including the LEDs that are driven on the basis of an output signal from the control signal generation circuit and expose the head with a light beam,
wherein:
the control signal generation circuit includes
a first band-pass filter (BPF 1) configured to pass a frequency band including a part of a band of θ waves and a part of a band of α waves,
an automatic gain control (AGC) limiter configured to suppress fluctuation in amplitude of the brain waves that depends on each individual,
a second band-pass filter (BPF 2), and
a feedback function of feeding back an output of the second band-pass filter (BPF 2) to the AGC limiter.
2. The photic stimulation device for the head according to claim 1, further comprising, as circuits that constitute the feedback function:
an absolute value circuit configured to output an absolute value of an input;
a BEF circuit (Band-Elimination Filter) configured to suppress an amplitude of an input; and
an low pass filter (LPF) circuit configured to filter an output of the BEF circuit.
3. The photic stimulation device for the head according to claim 2, wherein the frequency band is a continuous frequency band of 7 Hz to 13 Hz.
4. The photic stimulation device for the head according to claim 1, further comprising a pulse width modulation (PWM) unit configured to perform PWM modulation on an output of the control signal generation circuit, wherein the light exposing unit is driven on the basis of an output signal from the PWM modulation unit.
5. The photic stimulation device for the head according to claim 1, further comprising a memory adapted to have stored therein brain waves of an individual or a waveform that has been shaped from the brain waves of an individual, wherein waveform processing is performed on the basis of the waveform read from the memory.
6. The photic stimulation device for a head according to claim 1, wherein the photic stimulation device is configured to irradiate a head of a test subject with a red pulse beam, and further wherein:
the light exposing unit includes
a cap-like member having a number of red LEDs arranged thereon, and
an eye protection plate slidably provided on the cap-like member,
the eye protection plate is adapted to be, when the head is exposed with a light beam, slid to a position to cover eyes so as to protect the eyes, and
the eye protection plate is adapted to be positioned between the light exposing unit and a to-be-exposed region when slid back from a direction of the eyes.

7. The photic stimulation device for a head according to claim 1, wherein the photic stimulation device is configured to expose a head of a test subject to a red pulsed beam, and further wherein:
the photic stimulation device for the head is provided with a light guide path through which a part of a light beam in a housing of the device is guided to eyes of the test subject as an operation monitoring beam.

8. The photic stimulation device for the head according to claim 7, further comprising an adjustment switch configured to adjust or shield the operation monitoring beam.

9. A computer-implemented method for causing a computer to execute photic stimulation of a head of a test subject, the computer-implemented method comprising:
a control signal generation step of generating a control signal to control drive of LEDs on the basis of an output signal from a brain wave amplifier that performs A/D conversion on brain waves of an individual acquired with a sensor and amplifies the brain waves; and
a light irradiation step of irradiating the head with a light beam from the LEDs that are driven on the basis of an output in the control signal generation step,
wherein:
the control signal generation step includes
a process of a first band-pass filter (BPF 1) configured to pass a frequency band including a part of a band of θ waves and a part of a band of α waves,
a process of an automatic gain control (AGC) limiter configured to suppress fluctuation in amplitude of the brain waves that depends on each individual,
a process of a second band-pass filter (BPF 2), and
a step of feeding back an output of the process of the second band-pass filter (BPF 2) to the AGC limiter.

10. The computer-implemented method according to claim 9, further comprising, as the feeding-back step:
an absolute value output step of outputting an absolute value of an input;
a BEF output step of suppressing an amplitude of an input (Band-Elimination Filter output step); and
an low pass filter (LPF) step of filtering an output of the BEF output step.

11. The computer-implemented method according to claim 9, further comprising a PWM modulation step of performing pulse width modulation (PWM) on an output of the control signal generation step, wherein the light irradiation step is driven on the basis of an output signal from the PWM modulation step.

12. The computer-implemented method according to claim 9, wherein the frequency band is a continuous frequency band of 7 Hz to 13 Hz.

13. The computer-implemented method according to claim 9, further comprising a step of performing waveform processing on the basis of a waveform read from a memory adapted to have stored therein brain waves of an individual or a waveform that has been shaped from the brain waves of an individual.

14. A non-transitory, computer-readable recording medium containing instructions to carry out the computer-implemented method according to claim 9.

* * * * *